United States Patent [19]
Zimmer

[11] Patent Number: 5,310,555
[45] Date of Patent: May 10, 1994

[54] ORAL NUTRITIONAL AND DIETARY COMPOSITION

[75] Inventor: William Zimmer, Hollandale, Wis.

[73] Assignee: Midwestern Bio-Ag Products and Services, Inc., Blue Mounds, Wis.

[21] Appl. No.: 920,104

[22] Filed: Jul. 24, 1992

[51] Int. Cl.$^5$ .............................................. A23K 1/18
[52] U.S. Cl. ..................................... 424/438; 424/451; 424/453; 424/454; 424/456; 426/807
[58] Field of Search ............... 424/438, 451, 453, 454, 424/456; 426/807

[56] References Cited

U.S. PATENT DOCUMENTS

| | | | |
|---|---|---|---|
| 1,419,618 | 6/1922 | Deming | 424/451 |
| 1,815,902 | 7/1927 | Ellzey | 424/453 |
| 3,072,528 | 7/1958 | Kludas | 424/451 |
| 3,794,732 | 2/1974 | Raun | 424/283 |
| 3,839,557 | 10/1974 | Raun | 424/115 |
| 4,129,578 | 12/1978 | Celmer et al. | 260/345.7 R |
| 4,138,498 | 2/1979 | Das | 426/807 |
| 4,159,322 | 6/1979 | Cloyd | 424/181 |
| 4,405,609 | 9/1983 | Potter | 424/177 |
| 4,695,466 | 9/1987 | Morishita et al. | 424/456 |
| 4,761,426 | 8/1988 | Martin et al. | 514/460 |
| 5,104,662 | 4/1992 | Kalsta | 424/451 |

FOREIGN PATENT DOCUMENTS

| | | | |
|---|---|---|---|
| 2524311 | 10/1983 | France | 424/453 |
| 7610038 | 3/1978 | Netherlands | 424/454 |

OTHER PUBLICATIONS

Lund, A., *Yeasts and Moulds in Bovine Rumen*, Journal of General Microbiology (1974), vol. 81, 453–462.

Dawson, K., *Current and Future Role of Yeast Culture in Animal Production: A Review of Research Over the Last Six Years*, Biotechnology in the Feed Industry–Supplement to the Proceedings of Alltech's 8th Annual Symposium, pp. 1–23–surveys research from 1985–1991, publication date unknown, document shows 1992 award winner.

Brock & Madigan, *Biology of Microorganisms*, 6th Edition 1991, pp. 639–642.

Dawson, K., *Effects of Microbial Supplements Containing Yeast and Lactobacilli on Roughage-Fed Ruminal Microbial Activities*, J. Anim. Sci. (1990), vol. 68, pp. 3392–3398.

Gilliland, S. E., 8th Int'l. Biotech. Syn. Proc., vol. 2, pp. 923–933 (1988).

Aimutis, W. R., "Judging Microbials," *Feeds Management*, vol. 42, pp. 26–32 (1991).

Gedek, B., "Probiotics in Animal Feeding–Effects on Performance and Animal Health," *Feed Magazine International*, Feb. 1987.

Jones, B. E., "Hard Gelatin Capsules and the Pharmaceutical Formulator" *Pharmaceutical Technology*, vol. 9, Issue 9, p. 107 (1985).

*Primary Examiner*—Gabrielle Phelan
*Attorney, Agent, or Firm*—Stroud, Stroud, Willink, Thompson & Howard

[57] ABSTRACT

An oral nutritional supplement, i.e., a dietary adjunct, for livestock which includes incompatible live microbial cultures, and vitamin and mineral supplements, each separated from the other via multiple encapsulation. A method of delivering incompatible compounds in vivo, a method of preparing shelf-stable compositions of incompatible substances, and a system for delivering oral nutritional supplements to livestock are also provided.

11 Claims, 4 Drawing Sheets

ORAL NUTRITIONAL AND DIETARY COMPOSITION

TECHNICAL FIELD

This invention relates generally to nutritional and dietary compositions for livestock, and specifically to compositions which combine incompatible substances such as nutrient supplements and bacteria. The invention also relates to a method of preparing a shelf-stable composition of incompatible agents. The present invention is particularly well suited to deliver in vivo nearly simultaneously, incompatible supplements such as vitamins and minerals and bacteria to cattle, sheep and goats in the form of a capsule-in-a-capsule.

BACKGROUND OF THE INVENTION

In the past, the development of effective treatments for feeding disorders in cattle, sheep and goats has been spurred by a desire to maximize yields of meat and dairy products. Existing drug-based treatments (see, e.g., U.S. Pat. No. 4,761,426 issued to Martin, et al., and U.S. Pat. No. 4,405,609 issued to Potter), however, have the serious drawback of rendering products from treated animals unsalable for long periods under laws designed to protect consumers from harmful drug residues. Farmers, unhappy with the need to choose between low yields or unsalable products, have long sought the development of alternative, drug-free dietary treatments. The goals of drug-free dietary treatments are generally, improved growth and performance, and specially, appetite stimulation and reestablishment of the rumen bacterial populations necessary for proper digestion.

Much attention has been given in recent years to the use of certain microorganisms as dietary adjuncts in efforts to improve the growth and performance of livestock, and reestablishment of rumen bacterial populations. Such dietary cultures are known as probiotics or direct-fed microbials. (Gilliland, S. E., 8th Int'l. Biotech. Syn. Proc., Vol. 2, pp. 923-933 (1988)). Generally, the microorganisms of such probiotics are those that are expected to grow and/or function in the intestinal tract or rumen of the animal and can exert certain metabolic actions that influence the animal. Various microorganisms which have been considered for this type of usage include *Lactobacillus acidophilus, Lactobacillus plantarum, Lactobacillus fermentum, Lactobacillus casei,* and *Streptococcus faecium.*

To derive maximum benefit from use of probiotics, the microorganisms must survive and grow in the intestine. It is thus imperative that the probiotic contain viable and active microorganisms at the time of consumption. The bacteria used as probiotics, therefore, must be stable during preparation and during storage prior to consumption.

The simplest approach to delivery of probiotics is to add cultures to animal feed. However, it appears that few direct-fed microbials are stable in feed for more than 3-5 days. (Aimutis, W. R., *Feeds Management,* Vol. 42, pp. 26-32 (1991)). Moreover, some feed contains antibiotics which are contrary to microbials stability. Yet other feed is pelleted, and most Lactobacillus species, which are predominant and beneficial intestinal species, are susceptible to the high temperatures, compression, aeration and mixing abrasion to which they are exposed during the pelleting process.

Another approach is to provide the bacteria themselves as a pellet or bolus. Many such bolus products are commercially available.

More recently, bolus or pellet formulations have been developed which include a combination of the bacteria and dry vitamin and trace mineral supplements, as nearly simultaneous administration in vivo of these components has been suggested as being highly beneficial to achieving the goals of appetite stimulation and bacterial population reestablishment. Many of these bolus formulations are available commercially. It has been found, however, that the supplements and bacteria are incompatible as the vitamin and mineral levels efficacious for livestock are toxic to the bacteria. As indicated previously, microorganisms are also sensitive to mixing abrasion, aeration, compression and high temperatures, all of which occur during conventional hard bolus production. Moreover, the bolus formulations also require binding, wetting and disintegrating agents, any or all of which may adversely affect the viability of the bacteria. Such bolus products, therefore, have limited shelf stability in that the population of viable bacteria is greatly reduced within about a week.

Thus, a persistent and vexatious problem, largely unattended by the prior art, is the lack of a method for simultaneously delivering incompatible substances in vivo to animals, particularly when one of the substances is a viable microorganism culture.

Various prior art methods of physical separation, e.g., encoating, encapsulation and microencapsulation, of nutritional supplements are known, however, none adequately address the preparation and storage requirements of sensitive direct-fed microbial agents. For example, conventional microencapsulation subjects bacteria to a number of potentially fatal packaging procedures and requires expensive materials, complex equipment, and carefully controlled environmental conditions. Polymeric microcapsules also require specific pH ranges or enzyme activities to effect release of their contents in vivo. These requirements often frustrate conventional laboratory assessment techniques and prevent effective nutrient release in animals whose rumen pH or enzyme balances have been disrupted by bacterial depopulation.

U.S. Pat. No. 4,695,466 to Morishita discloses a multiple-encapsulation method. The Morishita process includes successively encapsulating oil solutions or suspensions in soft capsules. Although the method of Morishita has potential for delivery of two components in a single vehicle, the use of oil carriers presents insurmountable obstacles to the delivery of bacteria and vitamin supplement components. It is unlikely that Morishita's soft outer capsules will be able to withstand common shipping, storage and administration conditions and also is unlikely applicable to commonly available microbial forms.

Despite recognition of the known drawbacks of prior art products, the art has not adequately responded to date with a method for delivery in vivo of the incompatible components, namely, direct-fed microbials and nutrient supplements nearly simultaneously to cattle, sheep and goats.

SUMMARY OF THE INVENTION

The present invention responds specifically to the long-felt need heretofore unmet by the prior art, and especially with a view to overcoming the inherent inadequacies of combination supplements and direct fed microbials for oral delivery to animals. The composition is a dietary adjunct or feedstuff, providing the convenience and reliability of oral administration, while providing near simultaneous delivery in vivo of incompatible substances. The composition is shelf stable, i.e., allows substantially greater viability of microbials, and does not require binding, wetting and disintegrating agents necessary for pellet or bolus formulations.

The foregoing, and other advantages of the present invention, are realized in one aspect thereof in an oral nutritional composition, i.e., a dietary adjunct, useful for treating feeding disorders and improving feed efficiency in livestock, e.g., cattle, sheep and goats, especially ruminants. The dietary adjunct composition comprises a double capsule which includes live cultures of rumen bacteria in a first capsule which is enclosed with vitamin and mineral supplements in a second capsule. The capsules are preferably made of gelatin. The bacteria and supplements may be combined with acceptable feed grade carriers.

In another aspect, the invention is a method of simultaneously delivering incompatible compounds to animals in vivo. Such delivery is achieved by feeding an animal a double capsule containing a first substance in a first capsule, which is enclosed with a second substance, incompatible with the first substance, in a second larger capsule.

In another embodiment, this invention provides a method for preparing shelf-stable compositions of incompatible substances, which includes the use of multiple capsules of variable composition. Such method is accomplished manually or by machine.

Other advantages and a fuller appreciation of the specific adaptations, compositional variations, and physical and chemical attributes of the present invention will be gained upon an examination of the following detailed description of the invention, taken in conjunction with the accompanying drawings and appended claims.

BRIEF DESCRIPTION OF THE DRAWINGS

The present invention will hereinafter be described in conjunction with the appended drawings, wherein like designations refer to like elements throughout and in which.

DETAILED DESCRIPTION

Figure 1:
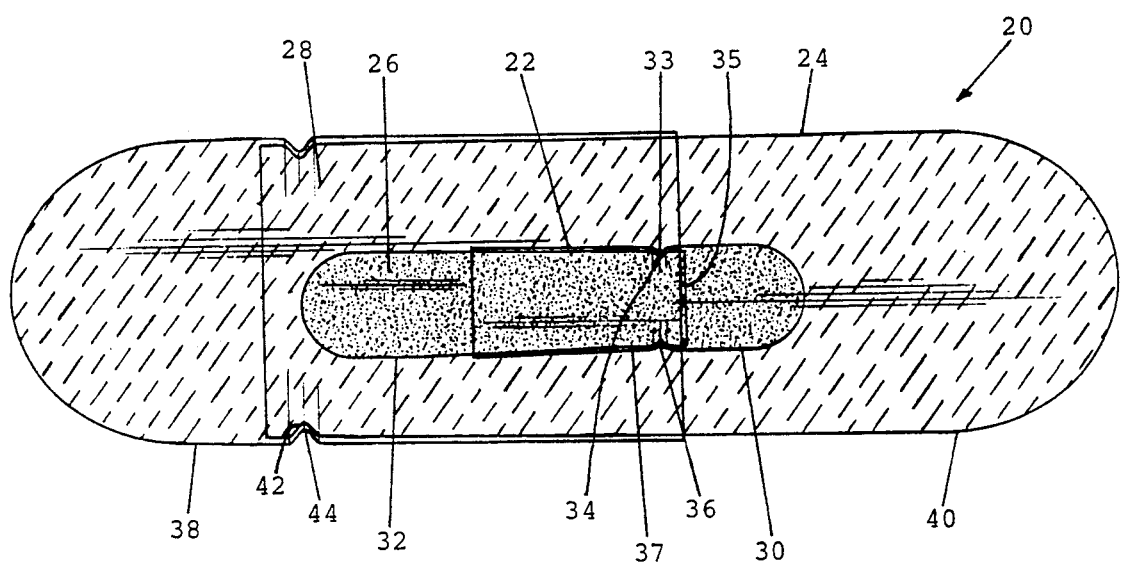
FIG. 1 shows an enlarged sectional view of the capsule-in-a-capsule structure in accordance with the present invention.
Figure 2B:
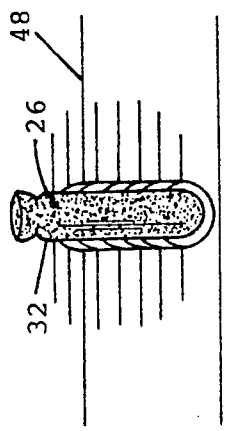
FIGS. 2a-2f illustrate a method by which each capsule-in-a-capsule is assembled.
Figure 2D:
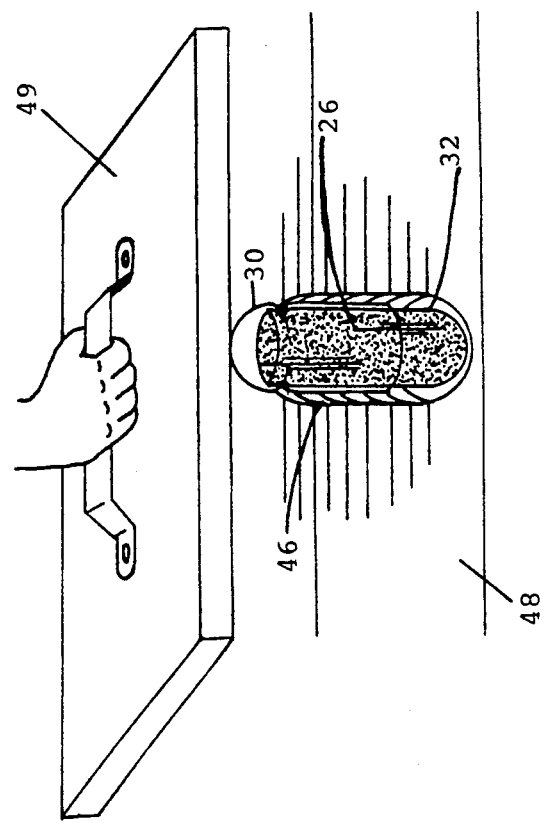
Figure 2A:
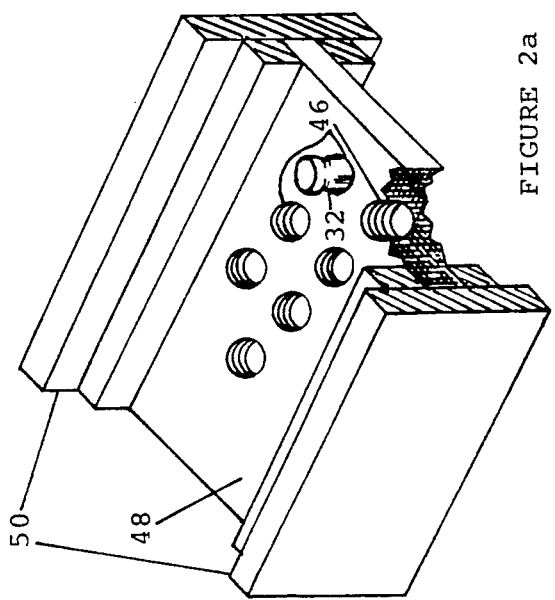
Figure 2C:
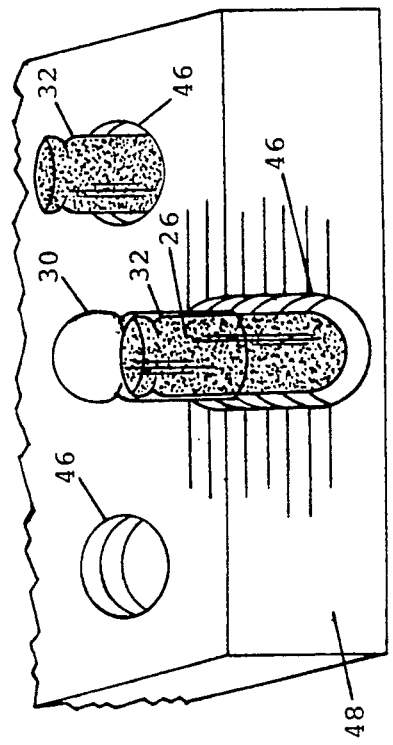
Figure 2E:
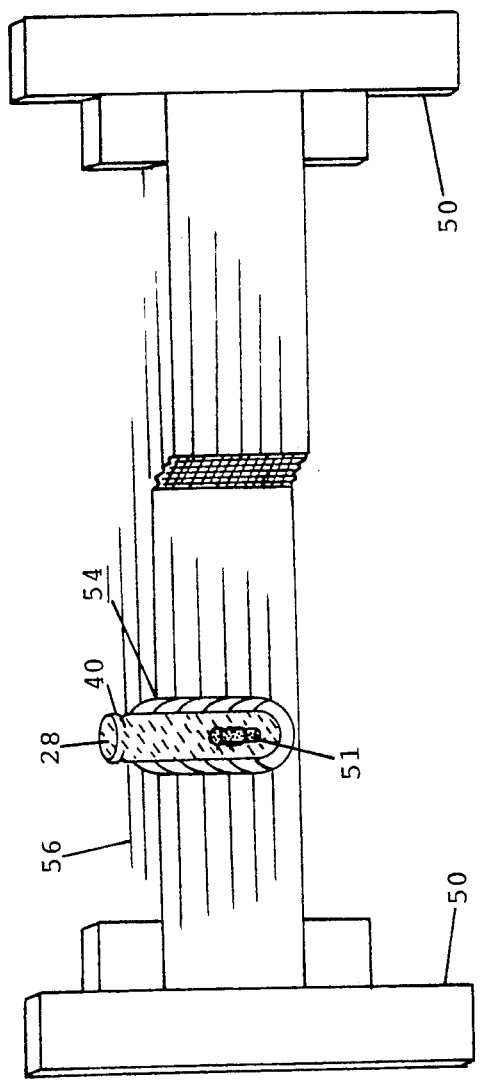
Figure 2F:
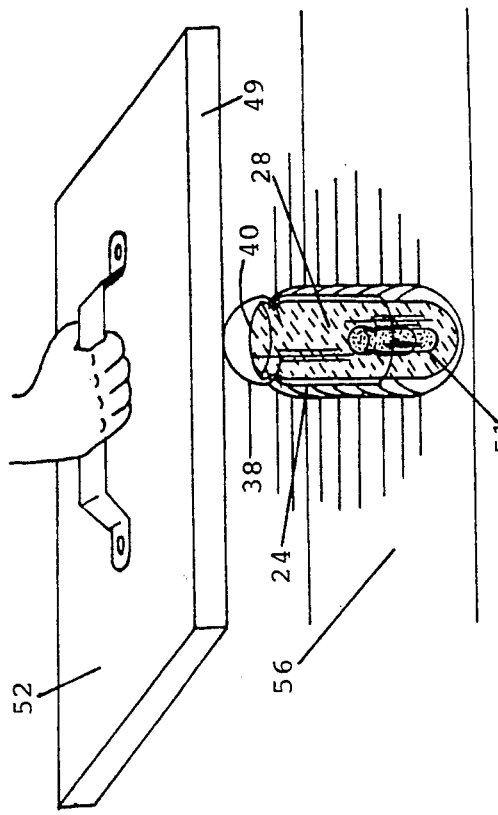

The present invention relates broadly to nutritional supplements and dietary adjuncts for animals, such as cattle, sheep and goats, and specifically to compositions and nutrient delivery systems which permit delivery of incompatible substances. However, the composition of the present invention is most particularly adapted for use in oral supplementation formulations which combine nutrients, such as vitamins and minerals, and viable microbials, such as rumen bacteria. Accordingly, the present invention will now be described in detail with respect to such fields of endeavor; however, those skilled in the art will appreciate that such description of the invention is meant to be exemplary only and should not be viewed as limitative of the full scope thereof.

The present invention provides a nutritional composition useful for ameliorating drug-induced, stress-related, and other feeding disorders in food-producing animals, e.g., cattle, sheep and goats. The composition is particularly useful as a ruminant feedstuff for improving feed efficiency and promoting growth. The composition avoids the milk and slaughter withdrawal periods required after drug treatments and enhances the general nutritional status of the animal. Additionally, the composition is shelf-stable and provides a general packaging system for incompatible materials, and is particularly useful for direct-fed microbial agents or probiotics. These attributes are achieved through a particular composition meeting a special combination of physical parameters.

As used herein, the term "incompatible" is meant to refer to substances which deleteriously react with one another when combined in desired levels or concentrations.

In one embodiment, the invention provides a nutritional composition whose components are mutually incompatible, and which incompatible components are physically separated from each other until they reach their in vivo situs. In a preferred embodiment, the composition includes components which are cultures of viable bacteria, and nutritional supplements, e.g., vitamins and minerals. As the cultures and nutritional supplements are incompatible, the microbial cultures are enclosed in a first capsule which is then enclosed with the vitamin and mineral supplements in a second such capsule, i.e., a "capsule-in-a-capsule" structure. The bacteria of the first component serve the valuable function of repopulating the rumen, thus enabling digestion to resume, producing digestive enzymes, and correcting acid imbalances which result from rumen bacterial depopulation.

The vitamins and minerals of the second component increase the nutritional status of animals laboring under conditions of malnutrition caused by feeding disorders. Further, once dispersed throughout the rumen, these vitamins and minerals support the rapid growth of the bacteria of the first component. Oral administration of these vitamins and minerals contemporaneously with the administration of bacteria is preferable to separate or intravenous administration. Separate administration increases the risk that bacteria will not encounter dispersed vitamins and minerals in the rumen and thus fail to exhibit their full growth potential.

It has been found that the bacterial survival rate with the capsule-in-a-capsule structure of the present invention after up to six months storage, i.e., six months after preparation, is nearly 500 times that of an admixture of the bacteria and nutrient supplements. An admixture of bacterial and nutrient supplements is typically a single capsule or a bolus formulation.

FIG. 1 illustrates a capsule-in-a-capsule structure in accordance with the present invention and is generally designated as 20. Capsule-in-a-capsule 20 includes an inner capsule 22 and an outer capsule 24. Inner capsule 22 contains viable bacteria 26 and outer capsule 24 contains vitamins and minerals generally designated as 28. Inner capsule 22 includes a top member 30 and a bottom member 32 which is bigger than top member 30. Top member 30 and bottom member 32 are locked together after filling by a locking mechanism 33 which includes a groove 34 proximate the top 35 of bottom portion 32 and a complementary ridge 36 substantially about the midportion 37 of top portion 30, forming a circumferentially nested ridge and groove. Similarly, outer capsule 24 has a top member 38 and a bottom member 40 in which top member 38 is locked to bottom member 40 with a groove 42 and a ridge 44. The capsules are preferably made of gelatin. Capsule shells are, however, easily reformulated to meet a myriad of size, transportation, storage, and administration requirements, e.g., excessive heat or cold, vibration, humidity, compression or impact, aeration, or ultraviolet light.

The bacteria of the first component, i.e., of inner capsule 22, include one or more of the indigenous intestinal bacteria selected from *Lactobacillus acidophilus, Lactobacillus lactis, Lactobacillus casei, Streptococcus faecium,* and *Pediococcus cerevisiae.* The bacteria can be processed in accordance with conventional methods of bacteriology to produce direct-fed microbial agents suitable for encapsulation in gelatin-shelled capsules and administration to cattle, sheep and goats. The in vitro viability of the bacteria of the inner capsule is determined by counting the colony-forming units per gram (CFU/g) of the culture administered, according to standard feed industry protocols. At time of preparation, the bacterial count in the inner capsule in accordance with the present invention is suitably about $20 \times 10^9$ CFU/g.

The bacteria can be employed in admixtures with conventional excipients, e.g., acceptable feed grade carriers suitable for enteral (e.g. oral) administration which do not deleteriously react with the bacteria. Suitable feed grade carriers include, but are not limited to, calcium carbonate, nonhygroscopic whey, rice hulls, and sucrose.

The bacterial preparations can also be mixed with auxiliary agents, e.g., whole dried milk, dextrose, enzymes, plasma proteins or amino acids to promote the growth and nutritional status of the animal and the bacteria in vivo.

The vitamins and minerals of the second component, i.e., outer capsule, are selected from one or more vitamins, namely, A, $B_{12}$, C, D, E, and K, niacin, thiamine, choline, biotin, folic acid, riboflavin, pantothenic acid, and one or more minerals, namely, cobalt, copper, iron, manganese, selenium and zinc.

The vitamins and minerals of the outer capsule 28 can be processed in accordance with conventional methods of pharmacy to produce agents suitable for encapsulation in gelatin-shelled capsules and administration to cattle, sheep and goats. For example, the vitamins and minerals can be administered in alternative sulfate, oxide, chelated, or other chemical forms to promote efficient dissolution and absorption in vivo.

The vitamins and minerals can also be employed in admixtures with conventional excipients, e.g., acceptable feed grade carriers which do not deleteriously react with them. Suitable carriers include, but are not limited to, antioxidants, flavoring agents, cellulose, grain by-products, or other inert vegetable materials. Nutrient-rich, dried organic materials, such as kelp, are highly preferred carrier materials, as they contribute significantly to the vitamin and mineral status of the animal and rumen bacteria.

The capsule-in-a-capsules for adult cattle are suitably prepared in 15 g double capsules and capsule-in-a-capsules for calves are suitably prepared as 4.5 g double capsules. Both sizes of capsules are orally administered daily as 1-2 capsule-in-a-capsule for three consecutive days at freshening or other signs of stress or feed distress.

It will be appreciated, however, that the actual preferred amounts of the compounds in the inner and outer capsules will vary according to the age, weight and species of animal being treated, and the particular feeding disorder of interest. For example, the amounts of vitamins and minerals in outer capsules for calves is suitably one-third of that in outer capsules for adult cattle. Feed guidelines can be determined by means of an appropriate conventional dietary protocol.

In another embodiment, the invention provides a method for simultaneously delivering incompatible substances to livestock in vivo. Specifically, the method includes oral administration of a capsule-in-a-capsule which structure includes a first gelatin-shelled capsule containing a first substance and a second gelatin-shelled capsule encapsulating the first capsule that contains a substance incompatible with the first. When the first substance is a bacterial culture of rumen bacteria, such method delivers at least $3 \times 10^9$ CFU/capsule-in-a-capsule.

The method in accordance with the present invention advantageously preserves the activity of mutually reactive or otherwise incompatible substances by physically separating them during production, storage and administration. When live microorganisms are administered to animals simultaneously with vitamins and minerals in bolus or single capsule formulations, the microorganisms often are rendered nonviable. The present method advantageously facilitates the consolidation of multistep therapies into easily administered, single-step therapies. Such efficient administration eliminates the stresses induced by the sequential administration of multi-phase treatment components and ensures the delivery of correct unit doses. The capsule-in-a-capsule vehicle is suitably delivered by hand or balling gun to cattle, sheep and goats.

In another aspect, the invention is an oral nutritional supplement delivery system for livestock. The system is a two-component system which effects near simultaneously delivery of the two components. The system comprises a first capsule containing at least one live microorganism and a second capsule enclosing both the first capsule and an admixture of vitamins and minerals, incompatible with live microorganisms. The capsules physically separate the incompatible microorganism cultures and nutrient supplements, thereby eliminating the need for separate administration of the microorganisms and the vitamin and mineral admixture.

To fabricate a capsule-in-a-capsule in accordance with the present invention, a first capsule, typically a gelatin capsule, is filled with a first substance and capped. This first capsule is placed inside the bottom member of a second, larger capsule, typically also a gelatin capsule, and the second capsule is then filled with a second substance, incompatible with the first substance, and capped. This method for efficiently and inexpensively preparing a shelf-stable composition of incompatible substances constitutes another aspect of the invention. The steps may be performed manually or by machine. This method of fabrication has certain production economics compared to production of hard boluses.

Reference is now made to FIGS. 2a-2f which illustrate a method of preparing the capsule-in-a-capsule formulation of the present invention. Specifically, the larger bottom members 32 of the inner, smaller capsules 22 are first placed in openings 46 in an assembly board 48 in a housing 50. Each bottom shell 32 is then filled with the bacterial culture 26. Top member 30 is then placed on each bottom member 32 and "locked" in place by using a mechanism which is the same or similar to locking mechanism 33 described hereinbefore by gentle pressure from pressboard 49 to form a sealed capsule 51. Filled sealed capsules 51 are ejected from the board 48, and the board 48 is removed from the housing 50.

A second assembly board 56, having holes 54, corresponding to the bottom members 40 of larger capsules 24, is placed in the machine housing 50. The bottom members 40 of the larger capsules 24 are placed in the board 56, and one sealed capsule 51 containing the bacteria is placed within each. The remaining volume of each bottom member 40 of capsule 24 is then filled with the vitamin and mineral admixture 28. A top member 38 is then placed over each bottom member 40 and locked as described previously in place with gentle pressure from the pressboard 52. The resulting capsule-in-a-capsule is then ejected from the second board 56.

Capsule-in-a-capsules can also be fabricated by machine using, e.g., a Torpac Capsule Filling Machine commercially available.

This fabrication method can be used to produce significantly more stable probiotics than conventional bolus or single-capsule delivery systems which combine sensitive bacteria with toxic levels of vitamins and trace minerals. The use of a multiple capsule also facilitates the administration of higher, more efficacious doses of vitamins and minerals than are delivered by conventional boluses. Further, gelatin-shelled capsules are efficiently and inexpensively assembled, thereby incurring reduced production costs relative to microencapsulation or hard bolus vehicles. The contents of such capsules also are not subjected to extremes of temperature, pressure or abrasion during their manufacture, thereby facilitating the consolidation of multi-step therapies utilizing components sensitive to such conditions.

Finally, capsule shells which are easily reformulated to provide particular protection to enclosed materials (e.g., different sized capsules or ultra-violet light filtering capsules) may be used interchangeably and in concert with other capsule shells of standard feed grade composition. In contrast, microencapsulation equipment cannot accommodate frequent coat or nutrient composition reformulations without costly equipment changes.

The present invention is further explained by way of the following examples which are to be construed as merely illustrative, and not limitative, of the remainder of the disclosure in any way whatsoever. In the following examples, all temperatures are expressed in degrees Celsius. All test capsules were randomly selected for analysis, and microorganisms were enumerated using the National Feed Ingredient Association's Standard Practice for the Enumeration of Microorganisms from Direct-Fed Microbials and Silage Innoculants. Bacterial viability is expressed in colony-forming units per gram of source material (CFU/g) or CFU per capsule.

EXAMPLE 1

Preparation of Capsule-in-a-Capsule

Capsule-in-a-capsule vehicles appropriated for administration to adult cattle were prepared by the method as described hereinbefore. The bacterial cultures were commercial formulations of dormant *Lactobacillus acidophilus, Lactobacillus lactis, Lactobacillus casei, Streptococcus faecium,* and *Pediococcus cerevisiae* having a viability of $20.0 \times 10^9$ CFU/g at the time of preparation. The vitamin and mineral admixture contained the following in the amounts indicated in parentheses: vitamin A ($5 \times 10^5$ IU), vitamin D ($7.5 \times 10^4$ IU), vitamin E (750 IU), vitamin $B_{12}$ (2000 μg), niacin ($3 \times 10^3$ μg), pantothenic acid (15 μg), choline (750 μg), biotin (75 μg), cobalt (20 μg), copper (none), iron (30 μg), manganese (30 μg), zinc (75 μg), and trace quantities of riboflavin, thiamine, folic acid, vitamin K, vitamin C, and selenium. Each capsule-in-a-capsule contained approximately 0.25 g of bacterial culture and 12.5 g of the vitamin and mineral admixture, the above-enumerated vitamins and minerals having been combined with kelp, an acceptable and nutrient-rich feed grade carrier.

Capsule-in-a-capsule vehicles appropriate for administration to calves were prepared by an identical method, excepting that the vitamin and mineral admixture contained approximately one-third of the amounts of the vitamins and minerals enumerated above for use in the adult cattle capsule-in-a-capsules. Each calf-size capsule-in-a-capsule contained approximately 0.25 g of bacteria culture and 3.5 g of the vitamin and mineral admixture, the vitamins and minerals having also been combined with kelp. Capsule-in-a-capsule vehicles identical to those of Example 1 were used in the following tests.

EXAMPLE 2

Determination of the Efficacy of Capsule-In-A-Capsule for Preserving the Viability of Anaerobic Bacterial Colony Forming Units Capsule-in-a-capsule vehicles appropriate for administration to adult cattle as described in Example 1 were variously tested against single capsule forms with an admixture of cultures and nutrient supplements as used in the adult cattle capsule-in-a-capsule form. All capsules were stored at room temperature for one week following their preparation. The capsule-in-a-capsules were randomly apportioned to two experimental groups, A and B. The single capsules enclosing admixed microbes and nutrient supplements comprised group C, and group D (control) comprised an unencapsulated sample of the microbial culture.

Inner capsule contents of four group A samples, outer capsule contents of one group B sample (to test the microbial content of the nutrient mixture), capsule contents of one group C sample, and nine of the group D control culture were randomly selected for comparison. Each test sample was individually serially diluted in autoclaved 6.25 mM phosphate buffer at pH=7.2. One (1) ml aliquots of each dilution were transferred into separate sterile petri plates. Twenty (20) ml of sterile LMRS (Lactobacilli Man Rugosa Sharpe Agar), cooled to 44° C. to 46° C., were then added to each petri plate with swirling. The plates were covered and cooled to room temperature before being inverted and placed into GasPak TM anaerobic jars. The plates were incubated at 35° C. until colonies were readily discernable, approximately two to three days. Colonies were then counted using a Quebec colony counter.

These data and the bacterial survival rate are given in Table 1 below.

TABLE 1

Bacterial Viability of Capsule-In-A-Capsule

| Test Group | Theoretical Bacterial Count At Preparation, CFU/g | Bacterial Count, CFU/g, 1 Week After Preparation | Bacteria Survival, % |
| --- | --- | --- | --- |
| A | $23 \times 10^9$ | $23 \times 10^9$ | 100 |
| B | — | $6 \times 10^2$ | — |
| C | $23 \times 10^9$ | $<10^6$ | $<.21$ |
| D (control) | $23 \times 10^9$ | $23 \times 10^9$ | 100 |

These data indicate that the contents of intact, gelatin-shelled capsule-in-a-capsules successfully retain 100% of their colony-forming activity after one week of storage at room temperature. Conversely, capsules which do not separate microbial cultures from nutrient supplement materials are not successful in protecting bacterial viability, and their contents lose 99.79% of their colony-forming activity within one week.

EXAMPLE 3

Determination of the Shelf Stability of Anaerobic Bacterial Colony Forming Units Packaged in Capsule-In-A-Capsules During Long-Term Storage at Room Temperature Capsule-in-a-capsules suitable for administration to adult cattle were fabricated as described above in Example 1 and stored at room temperature. At preselected intervals after their manufacture, i.e, one, two, three, four, five and six months, inner capsules containing the bacterial cultures were removed from randomly selected capsule-in-a-capsules. The contents of each inner capsule were serially diluted in autoclaved 6.25 mM phosphate buffer, pH=7.2, and 1 ml aliquots of each dilution were transferred into sterile petri plates. Twenty (20) ml of sterile LMRS Agar cooled to 44° C. to 46° C., were then added to each petri plate with swirling. The plates were covered and cooled to room temperature before being inverted and placed into GasPak TM anaerobic jars. The plates were incubated at 35° C. until colonies were readily discernable, approximately two to three days. Colonies were then counted using a Quebec colony counter. These data and the bacterial survival rates are given in Table 2 below.

TABLE 2

Shelf Stability of Capsule-In-A-Capsule

| Time After Manufacture, mos. | Bacterial Count, CFU/g | Bacterial Survival, % |
| --- | --- | --- |
| 1 | $22.5 \times 10^9$ | 100 |
| 2 | $20.0 \times 10^9$ | 89 |
| 3 | $21.2 \times 10^9$ | 94 |
| 4 | $16.1 \times 10^9$ | 72 |
| 5 | $13.0 \times 10^9$ | 58 |
| 6 | $12.0 \times 10^9$ | 53 |

These data indicate that sufficient bacteria remain viable in the capsule-in-a-capsule vehicle to repopulate the rumen after six months of storage under typical field conditions. In contrast, the number of CFU/g of conventional boluses approaches zero approximately three weeks after manufacture under similar conditions.

EXAMPLE 4

Determination of the Shelf Stability of Anaerobic Bacterial Colony Forming Units Combined with Vitamin and Mineral Supplements During Long-Term Storage at Room Temperature The shelf stability of single capsule formulations identical to the adult cattle capsule-in-a-capsule formulations of Example 1 were determined. Single gelatin-shelled capsules were filled with an admixture of the bacterial culture and vitamin and mineral supplement in a 1:39.55 gram:gram ratio present in the capsule-in-a-capsule vehicle of Example 1. The capsules were packed in ice for two days prior to testing; thereafter all capsules were stored at room temperature. A pure sample of the microbial culture was reserved on ice as a control.

At 2, 3, 4, 5, 8, 12, 16, 20, 25, and 32 days after manufacture, the contents of three randomly-selected capsules were nonabrasively combined, and samples therefrom were serially diluted in autoclaved 6.25 mM phosphate buffer at pH=7.2. During the initial analysis, a control sample from the microbial culture control was also diluted and analyzed. One (1) ml aliquots of each dilution were transferred in duplicate into separate sterile petri plates. Twenty (20) ml of sterile Lactobacillus MRS Agar, cooled to 44° C. to 46° C., were then added to each petri plate with swirling. The plates were covered and cooled to room temperature before being inverted and placed into GasPak TM anaerobic jars. The plates were incubated at 35° C. until colonies were readily discernable, approximately two to three days. Colonies were then counted using a Quebec colony counter.

These data and bacterial survival rates are given in Table 3 below.

TABLE 3

Shelf Stability of Single Capsules Equivalent to Capsule-In-A-Capsule

| Time After Manufacture, days | Bacterial Count, CFU/g | Bacterial Survival, % |
| --- | --- | --- |
| 2 | $21.0 \times 10^7$ | 56.7 |
| 3 | $4.5 \times 10^7$ | 12.1 |
| 4 | $10.0 \times 10^7$ | 27.0 |
| 5 | $119 \times 10^7$* | $>100$ |
| 8 | $10.0 \times 10^7$ | 27.0 |
| 12 | $15.0 \times 10^7$ | 40.5 |
| 16 | $42.0 \times 10^6$ | 11.3 |
| 20 | $31.0 \times 10^6$ | 8.3 |
| 25 | $26.0 \times 10^6$ | 7.0 |
| 32 | $27.0 \times 10^5$ | 0.7 |

*possible counting error

These data demonstrate that bacteria packaged directly with nutrient supplements lose nearly 50% of their colony-forming activity within two days of manufacture and nearly 100% of their colony-forming activity within 33 days of manufacture. Thus, the physical separation of the microbes and nutrients effected by the multiple capsule vehicle is responsible for the superior delivery of viable microbes after long-term storage demonstrated in Example 3.

EXAMPLE 5

Comparison of Anaerobic Bacterial Colony Forming Units Per Gram of Hard Bolus and Capsule-In-A-Capsule within their Expiration Period Bacterial viability of capsule-in-a-capsules in accordance with the present invention were compared with various commercially available hard boluses purporting to contain similar microorganisms and vitamins and minerals. The following products were tested and compared to the capsule-in-a-capsule formulation of the present invention (both adult cattle and calf-size formulations were tested):

| Product No. | Number of Samples Used | Product Description/Name |
|---|---|---|
| (cow size) | | |
| 01 | 2 | Present Invention (capsule-in-a-capsule) |
| 02 | 2 | Primilac TM Cattle bolus, Star Labs |
| 03 | 2 | Probiocin TM Bolus, Pioneer Hi-Bred International, Inc. |
| 04 | 1 | T.N.T. Stress Bolus, Tomorrow's Nutrition Today |
| (calf size) | | |
| 05 | 5 | Present Invention (capsule-in-a-capsule) |
| 06 | 4 | Equal-lizer, Med-Vet Pharma |
| 07 | 5 | Lactobols TM, United Agri-Sales |
| 08 | 4 | LactoPlus TM, Vet's Plus |
| 09 | 4 | LBA TM, Osborn/Int'l Multifoods |
| 10 | 4 | Problocin TM, Pioneer Hi-Bred International, Inc. |
| 11 | 4 | T.N.T. Stress Bolus, Tomorrow's Nutrition Today |

The above-described number of samples of each commercial bolus and capsule-in-a-capsule product were randomly selected from commercial shipments within their expiration periods. Boluses from each commercial brand were individually ground with a sterile mortar and pestle and then combined with the others of this brand. Each capsule-in-a-capsule was manually disassembled and the contents thereof combined with those of other disassembled capsule-in-a-capsules.

Twenty-two gram portions of each ground bolus mixture or disassembled capsule-in-a-capsule mixture, and 450 ml of sterile 6 mM phosphate buffer, pH=7.2, were blended for 1 min at low speed in a sterile stomacher bag. Each mixture was then serially diluted in additional phosphate buffer. Each dilution was plated in triplicate by placing a 1 ml aliquot in each of three sterile petri plates and adding 15 ml of 44°–46° C. MRS (Man Rugosa Sharpe) Agar to each plate with swirling. The plating procedure was then replicated for each dilution using LBS (Lactobacilli Sharpe) Agar and then MRSO (Man Rugosa Sharpe with 0.15% Oxgall) Agar. The plates were covered and cooled to room temperature, at which time 4 ml of 44°–46° C. tempered agar were applied to the plate surface. After the tempered agar solidified, the plates were inverted and placed in anaerobic jars for incubation at 32° C. for 72 hrs. Colonies on each plate were then counted according to standard methods.

The above-described procedure was repeated for a second, identically selected group of boluses and capsule-in-a-capsules, and the results of both studies were averaged to described the colony-forming potential delivered by each vehicle. The results are graphed in FIG. 3. Activity on MRS agar reflects the total activity attributable to anaerobic bacteria, while activity on LBS agar reflects the total activity attributable to lactic acid bacteria, the type of bacteria which the vehicles are intended to deliver. Activity on MRSO agar reflects the total activity of intestinal anaerobic bacteria, as the added Oxgall inhibits all but bile-resistant species.

Figure 3:
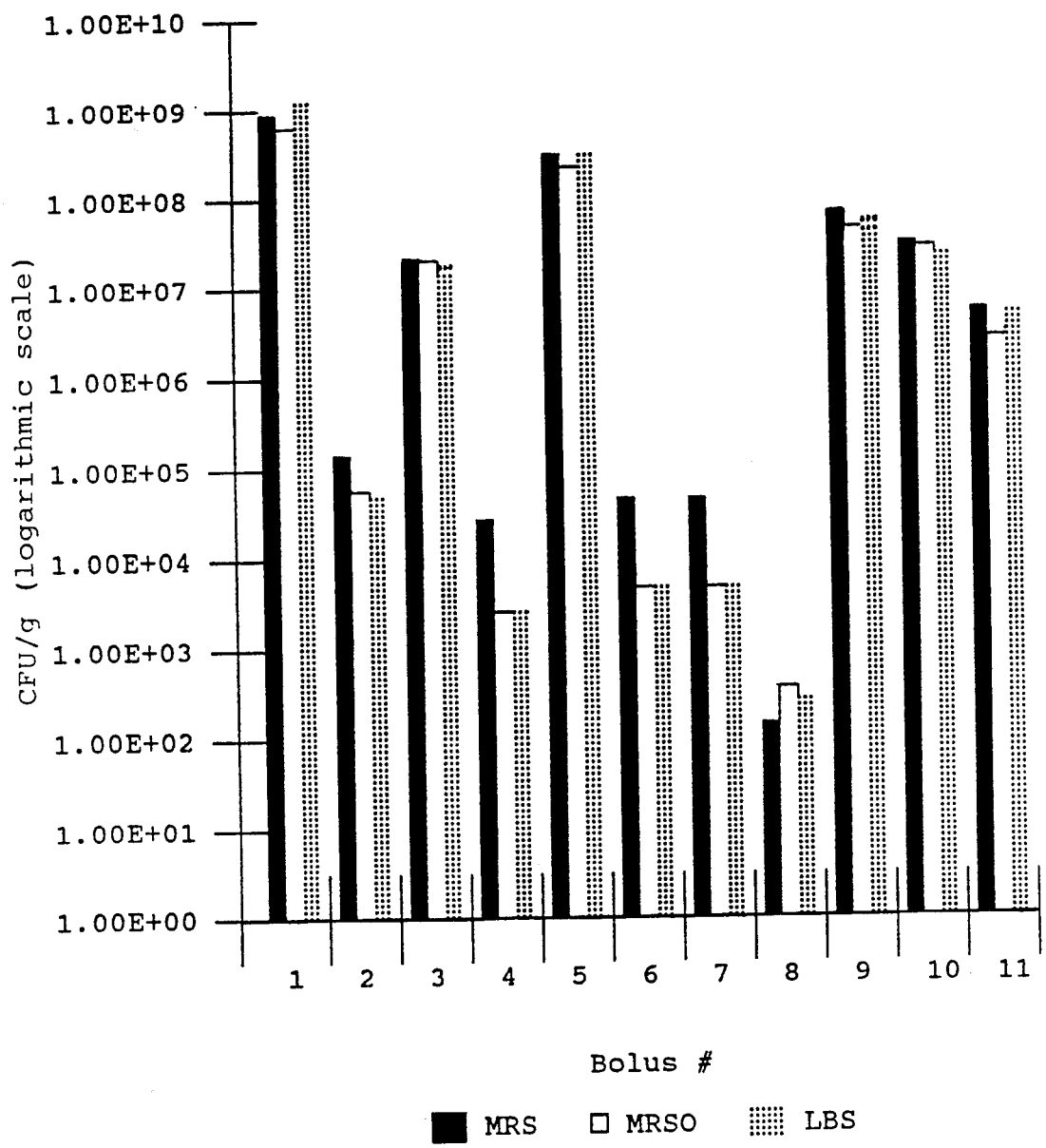
FIG. 3 compares the efficacy of double capsules in accordance with the present invention and hard boluses in simultaneously delivering live microorganisms and incompatible nutrient supplements.

These data illustrated in FIG. 3 indicate that use of the capsule-in-a-capsule delivery system facilitates the delivery of 13 times to 54 million times more lactic acid bacteria CFU/g than conventional hard boluses. These data further indicate that a minimum of 92% of the viable bacteria are the desired lactobacilli, and between 60 and 67% of those bacteria are bile-resistant species presumably capable of successfully repopulating the intestine.

EXAMPLE 6

Comparison of Capsule-In-A-Capsule and Standard Hard Bolus Dissolution Times in vivo Dissolution times in vivo for capsule-in-a-capsules in accordance with the present invention and commercially available hard bolus formulations were compared. Both adult cattle and calf-size formulations were tested. Randomly selected, intact capsule-in-a-capsules and the commercially available hard boluses of Example 5 were placed in nylon floss slings and lowered into separate 500 ml erlenmeyer flasks of fresh cow rumen contents. The flasks were maintained at 101.5° F. and a pH=6.35, without stirring. Samples were raised from the fluid for examination at regular intervals until complete dissolution was achieved, thereby establishing approximate dissolution times for each.

After the approximate dissolution times were established, a second sample of capsule-in-a-capsules and hard boluses were randomly selected from the groups of Example 5, placed in slings, and lowered into 500 ml erlenmeyer flasks of fresh cow rumen contents. These flasks were maintained at the above-described temperature and pH. Individual samples were examined at intervals ranging from 30 sec. to 30 min., according to the dissolution times previously established. Flask contents were examined to confirm complete dissolution when empty slings were observed. The dissolution times are given in Table 4.

TABLE 4

Comparison of Dissolution Times of Capsule-In-A-Capsule and Hard Boluses

| Product Number | Dissolution Time Trial 1 | Dissolution Time Trial 2 | Average Time, sec. | Average Time, min. |
|---|---|---|---|---|
| (cow size) | | | | |
| 01 (present invention) | 410 | 531 | 470.5 | 7.84 |
| 02 | 12720 | 12780 | 12750 | 212.50 |
| 03 | 2144 | 2170 | 2157 | 35.95 |
| 04 | 2227 | 2286 | 2256.5 | 37.61 |
| (calf size) | | | | |
| 05 (present invention) | 323 | 372 | 347.5 | 5.79 |
| 06 | 3632 | 5423 | 4527.5 | 75.46 |
| 07 | 10620 | 10680 | 10650 | 177.00 |
| 08 | 19380 | 22020 | 20700 | 345.00 |
| 09 | 22020 | 23160 | 22590 | 376.50 |
| 10 | 2472 | 2503 | 2487.5 | 41.46 |
| 11 | 2530 | 2549 | 2539.5 | 42.33 |

A mean dissolution time of both capsule-in-a-capsule test samples of 6.82 min was obtained for the gelatin-shelled capsule-in-a-capsules, while mean dissolution times for the hard boluses ranged from 36 to 376 min.

These data indicate that nutritional compositions delivered via capsule-in-a-capsule vehicles are virtually immediately available to distressed animals, while hard bolus contents may not become available for an extended period of time or may pass beyond the appropriate in vivo situs before dissolution.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

I claim:

1. A dietary adjunct composition comprising a double capsule, said double capsule including an inner capsule and an outer capsule spaced apart and enclosing said inner capsule;
    said inner capsule including a gelatin shell and live intestinal or rumen microorganisms therein, wherein said intestinal or rumen microorganisms are bacteria, wherein said bacteria are one or more of *Lactobacillus acidophilus, Lactobacillus lactis, Lactobacillus casei, Streptococcus faecium,* or *Pediococcus cerevisiae;*
    said outer capsule including a gelatin shell and a nutritional supplement therein, wherein said nutritional supplement is selected from the group consisting of vitamins, minerals, and a combination thereof;
        said vitamins including one or more of vitamin A, vitamin D, vitamin E, vitamin $B_{12}$, riboflavin, niacin, pantothenic acid, thiamine, choline, folic acid, biotin, vitamin K, and vitamin C, and
        said minerals including one or more of cobalt, copper, iron, manganese, zinc, and selenium.

2. The composition of claim 1, wherein said bacteria are present at a level of at least $3 \times 10^9$ CFU/capsule at the time of consumption.

3. The composition of claim 1, wherein said nutritional supplement is admixed with an acceptable feed grade carrier.

4. A dietary adjunct composition comprising a double capsule, said double capsule including an inner capsule and an outer capsule spaced apart and enclosing said inner capsule;
    said inner capsule including a gelatin shell and live intestinal or rumen microorganisms therein, wherein said intestinal or rumen microorganism are bacteria, wherein said bacteria are one or more of *Lactobacillus acidophilus, Lactobacillus lactis, Lactobacillus casei, streptococcus faecium,* or *Pediococcus cerevisiae;*
    said outer capsule including a gelatin shell and a nutritional supplement therein, wherein said nutritional supplement is selected from the group consisting of vitamins, minerals, and a combination thereof,
        said vitamins including one or more of vitamin A, vitamin D, vitamin E, vitamin $B_{12}$, riboflavin, niacin, pantothenic acid, thiamine, choline, folic acid, biotin, vitamin K, and vitamin C, and
        said minerals including one or more of cobalt, copper, iron, manganese, zinc, and selenium;
    wherein said nutritional supplement is admixed with an acceptable feed grade carrier, said feed grade carrier being kelp.

5. A method of delivering in vivo incompatible substances, comprising the steps of administering orally a double capsule having
    an inner capsule including
        a gelatin shell and
        a first substance therein, said first substance being a viable substance, said viable substance being bacteria, wherein said bacteria are one or more of *Lactobacillus acidophilus, Lactobacillus lactis, Lactobacillus casei, Streptococcus faecium,* or *Pediococcus cerevisiae,* and
    an outer capsule enclosing said inner capsule, said outer capsule including
        a gelatin shell and
        a second substance therein, wherein said second substance is vitamins, minerals, or a combination of both,
        said vitamins including one or more of vitamin A, vitamin D, vitamin E, vitamin $B_{12}$, riboflavin, niacin, pantothenic acid, thiamine, choline, folic acid, biotin, vitamin K, and vitamin C,
        said minerals including one or more of cobalt, copper, iron, manganese, zinc, and selenium;
    wherein said second substance is admixed with an acceptable feed grade carrier, wherein said feed grade carrier is kelp,
    said first substance rendered nonviable when said first substance and said second substance are administered simultaneously in a bolus or in a single capsule formulation.

6. The method of claim 5, wherein said administering step includes administering to an animal one to two of said double capsules daily for three consecutive days at freshening or during periods of stress.

7. A method of delivering in vivo incompatible substances, comprising the steps of administering orally a double capsule having
    an inner capsule including
        a gelatin shell and
        a first substance therein, said first substance being a viable substance, said viable substance being bacteria, wherein said bacteria are one or more of *Lactobacillus acidophilus, Lactobacillus lactis, Lactobacillus casei, Streptococcus faecium,* or *Pediococcus cerevisiae,* and
    an outer capsule enclosing said inner capsule, said outer capsule including
        a gelatin shell and
        a second substance therein, wherein said second substance is vitamins, minerals, or a combination of both,
        said vitamins including one or more of vitamin A, vitamin D, vitamin E, vitamin $B_{12}$, riboflavin, niacin, pantothenic acid, thiamine, choline, folic acid, biotin, vitamin K, and vitamin C,
        said minerals including one or more of cobalt, copper, iron, manganese, zinc, and selenium;
    wherein said second substance is admixed with an acceptable feed grade carrier, said feed grade carrier including kelp;
    said first substance being rendered nonviable when said first substance and said second substance are administered simultaneously in a bolus or in a single capsule formulation; and wherein said administering step includes administering to an animal one to two of said double capsules daily for three consecutive days at freshening or during periods of stress.

8. A dietary adjunct composition, comprising a double capsule, said double capsule including an inner capsule and an outer capsule spaced apart and enclosing said inner capsule, said inner capsule including a gelatin shell and live bacteria therein, said outer capsule having a gelatin shell and including vitamins, minerals or a combination thereof, said vitamins including one or more of vitamin A, vitamin D, vitamin E, vitamin $B_{12}$, riboflavin, niacin, pantothenic acid, thiamine, choline, folic acid, biotin, vitamin K, and vitamin C, said minerals including one or more of cobalt, copper, iron, manganese, zinc, and selenium, and said bacteria being one or more of *Lactobacillus acidophilus, Lactobacillus lactis, Lactobacillus casei, Streptococcus faecium* or *Pediococcus cerevisiae.*

9. The composition of claim 8, wherein said outer capsule includes an acceptable feed grade carrier.

10. The composition of claim 8, wherein said bacteria are present at a level of at least $3 \times 10^9$ CFU/capsule at the time of consumption.

11. A dietary adjunct composition, comprising a double capsule, said double capsule including an inner capsule and an outer capsule spaced apart and enclosing said inner capsule, said inner capsule including a gelatin shell and live bacteria therein, said bacteria being one or more of *Lactobacillus acidophilus, Lactobacillus lactis, Lactobacillus casei, Streptococcus faecium* or *Pediococcus cerevisiae;* said outer capsule having a gelatin shell and including vitamins, minerals or a combination thereof, said vitamins including one or more of vitamin A, vitamin D, vitamin E, vitamin $B_{12}$, riboflavin, niacin, pantothenic acid, thiamine, choline, folic acid, biotin, vitamin K, and vitamin C, said minerals including one or more of cobalt, copper, iron, manganese, zinc, and selenium, and wherein said capsule further includes a feed grade carrier, said carrier being kelp.

* * * * *

UNITED STATES PATENT AND TRADEMARK OFFICE
CERTIFICATE OF CORRECTION

PATENT NO. : 5,310,555
DATED : May 10, 1994
INVENTOR(S) : William A. Zimmer

Page 1 of 2

It is certified that error appears in the above-indentified patent and that said Letters Patent is hereby corrected as shown below:

Column 8, lines 7-10,

Delete: "vitamin $B_{12}$ (2000 µg), niacin ($3\times10^3$ µg), pantothenic acid (15 µg), choline (750 µg), biotin (75 µg), cobalt (20 µg), copper (none), iron (30 µg), manganese (30 µg), zinc (75 µg),".

And insert: --vitamin $B_{12}$ (2000 µg), niacin ($3\times10^3$ mg), pantothenic acid (15 mg), choline (750 mg), biotin (75 µg), cobalt (20 mg), copper (none), iron (30 mg), manganese (30 mg), zinc (75 mg),--.

In the specification, Column 9, lines 66-68,

Delete: "conditions. In contrast, the number of CFU/g of conventional boluses approaches zero approximately three weeks after manufacture under similar conditions.".

And insert: --conditions. In contrast, the Percent Bacterial Survival of conventional boluses approaches zero approximately four weeks after manufacture under similar conditions as shown in TABLE 3 of Example 4.--.

UNITED STATES PATENT AND TRADEMARK OFFICE
CERTIFICATE OF CORRECTION

PATENT NO. : 5,310,555
DATED : May 10, 1994
INVENTOR(S) : William A. Zimmer

It is certified that error appears in the above-indentified patent and that said Letters Patent is hereby corrected as shown below:

Column 12, line 10,

Delete: "CFU/g".

And insert: --CFU/Bolus--.

In the drawings, in FIGURE 3, in the figure caption,

Delete: "VIABLE BACTERIAL COUNTS PER GRAM".

And insert: --VIABLE BACTERIAL COUNTS PER BOLUS--.

In the drawings, in FIGURE 3, on the Y-axis caption,

Delete: "CFU/g".

And insert: --CFU/Bolus--.

Signed and Sealed this

Eleventh Day of June, 1996

Attest:

BRUCE LEHMAN

Attesting Officer

Commissioner of Patents and Trademarks